US007695506B2

(12) United States Patent
Thistle et al.

(10) Patent No.: US 7,695,506 B2
(45) Date of Patent: Apr. 13, 2010

(54) ATRAUMATIC CONNECTIONS FOR MULTI-COMPONENT STENTS

(75) Inventors: Robert C. Thistle, Bridgewater, MA (US); Kristian DiMatteo, Waltham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 271 days.

(21) Appl. No.: 10/946,199

(22) Filed: Sep. 21, 2004

(65) Prior Publication Data

US 2006/0064156 A1    Mar. 23, 2006

(51) Int. Cl.
*A61F 2/06*    (2006.01)

(52) U.S. Cl. ..................................... 623/1.16
(58) Field of Classification Search .................. 623/1.1, 623/1.13–1.22, 1.3–1.35, 1.27, 1.53, 1.23, 623/1.39–1.43; 403/292
See application file for complete search history.

(56) References Cited

U.S. PATENT DOCUMENTS

| | | | | |
|---|---|---|---|---|
| 5,383,892 | A * | 1/1995 | Cardon et al. | 623/1.16 |
| 5,817,126 | A * | 10/1998 | Imran | 623/1.15 |
| 5,938,695 | A * | 8/1999 | Borghi | 623/1.16 |
| 6,013,854 | A * | 1/2000 | Moriuchi | 623/1.11 |
| 6,063,101 | A * | 5/2000 | Jacobsen et al. | 623/1.11 |
| 6,174,330 | B1 * | 1/2001 | Stinson | 623/1.34 |
| 6,270,524 | B1 * | 8/2001 | Kim | 623/1.15 |
| 6,398,807 | B1 * | 6/2002 | Chouinard et al. | 623/1.35 |
| 6,485,510 | B1 * | 11/2002 | Camrud et al. | 623/1.16 |
| 6,585,758 | B1 * | 7/2003 | Chouinard et al. | 623/1.16 |
| 6,589,275 | B1 * | 7/2003 | Ivancev et al. | 623/1.15 |
| 6,648,911 | B1 | 11/2003 | Sirhan et al. | |
| 2002/0042645 | A1 * | 4/2002 | Shannon | 623/1.13 |
| 2003/0135266 | A1 * | 7/2003 | Chew et al. | 623/1.16 |
| 2003/0149473 | A1 * | 8/2003 | Chouinard et al. | 623/1.15 |
| 2003/0208256 | A1 * | 11/2003 | DiMatteo et al. | 623/1.11 |
| 2004/0015228 | A1 * | 1/2004 | Lombardi et al. | 623/1.18 |
| 2004/0098100 | A1 | 5/2004 | Williams et al. | |
| 2004/0106980 | A1 | 6/2004 | Solovay et al. | |
| 2005/0149171 | A1 | 7/2005 | McCullagh et al. | |
| 2008/0208319 | A1 * | 8/2008 | Rabkin et al. | 623/1.16 |

FOREIGN PATENT DOCUMENTS

WO    WO 00/27306    5/2000

OTHER PUBLICATIONS

International Search Report for International Application No. PCT/US2005/030921 dated Dec. 22, 2005.

* cited by examiner

*Primary Examiner*—Anhtuan T Nguyen
*Assistant Examiner*—Elizabeth Houston
(74) *Attorney, Agent, or Firm*—Brooks, Cameron & Huebsch, PLLC

(57) ABSTRACT

A stent is provided that includes at least two stent segments which mate with one another. At least one of the stent segments includes a hollow member, and at least one of the stent segments includes a solid member. At least one of the solid members is secured to at least one of the hollow members.

23 Claims, 6 Drawing Sheets

ATRAUMATIC CONNECTIONS FOR MULTI-COMPONENT STENTS

FIELD OF THE INVENTION

The present invention relates to stent connections which facilitate fastening of stent segments or which facilitate joining other stent-related functions together.

BACKGROUND OF THE INVENTION

Stents are generally tubular devices for insertion into body lumens. A stent is typically used to prop open a passageway or, in combination with a graft, provide a prosthetic intraluminal wall, e.g., in the case of a vascular stenosis or aneurysm, to provide an unobstructed conduit for blood in the area of the stenosis or aneurysm. A stent may be endoluminally deployed in a body lumen, a blood vessel for example, at the site of a stenosis or aneurysm by so-called "minimally invasive techniques" in which the stent is compressed radially inwards and is delivered by a catheter to the site where it is required, through the patient's skin, or by a "cut down" technique at a location where the blood vessel concerned is accessible. When the stent is positioned at the correct location, the stent is caused or allowed to re-expand to a predetermined diameter in the vessel.

Stents often consist of more than one component, and different securing means are known for securing stent elements together. For example, stent portions may be secured together via welds at one or more points or seams where the portions are immediately adjacent one another. Elements of individual stent segments may also be fastened to one another by crimping the elements together. In yet another example, stent portions may be secured together via a combination of crimping members and welds. This technique is described in U.S. application Ser. No. 10/748,444 filed Dec. 20, 2003, entitled, "CRIMP AND WELD CONNECTION," which is incorporated herein by reference.

Nevertheless, stent elements which facilitate connecting together stent segments or provide other functions would be useful.

SUMMARY OF THE INVENTION

Hollow members, constructed of hypo-tubes for example, are used as stent members. Other stent members may be secured to the hollow members either externally or internally.

A hollow stent member may also contain a drug for elution through an opening in the member or an imageable material to facilitate stent positioning.

DETAILED DESCRIPTION OF THE INVENTION

Figure 1:
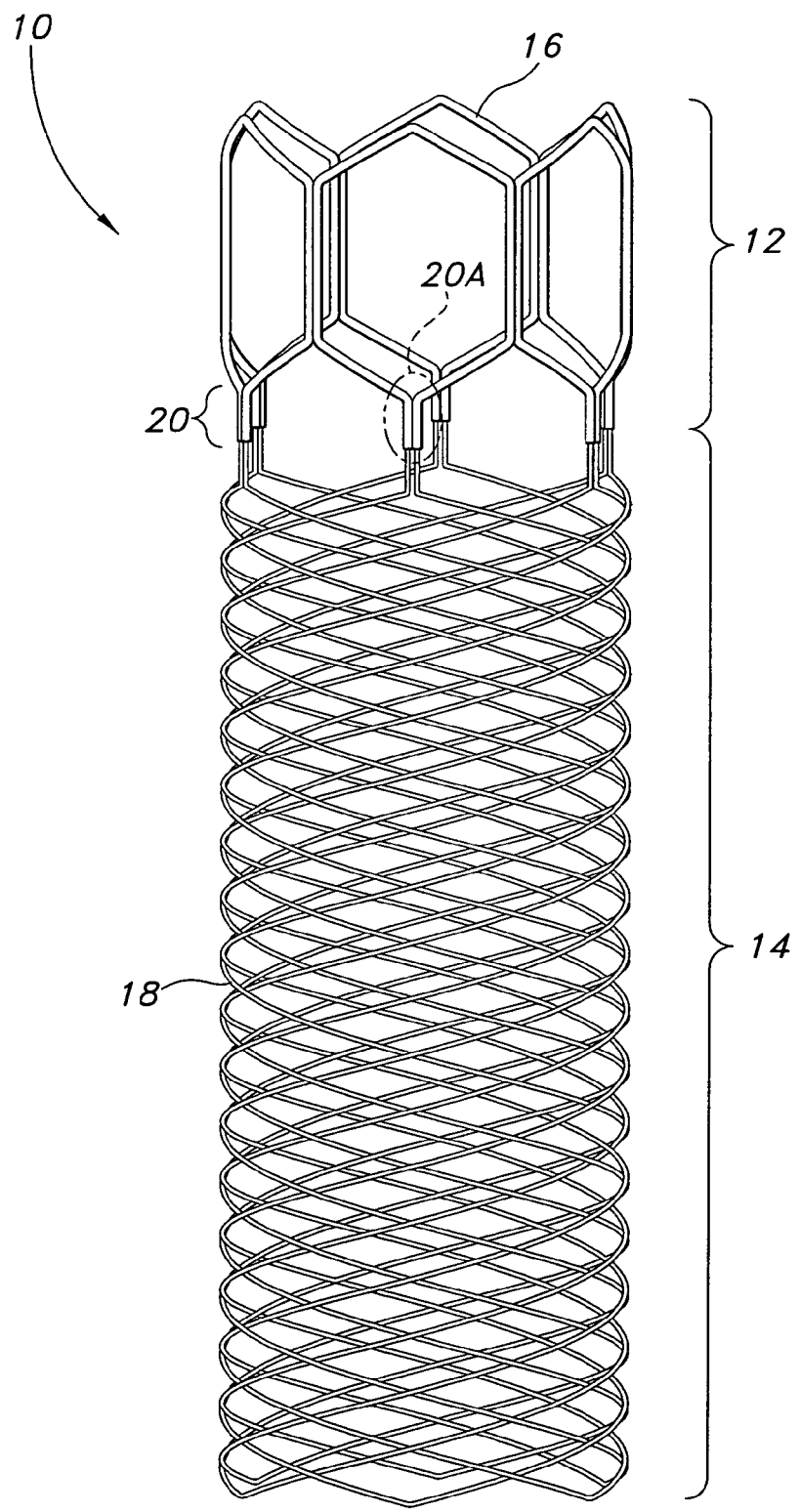
FIG. 1 illustrates a multi-component stent which utilizes hollow stent members as described herein.

Referring generally to FIG. 1, there is shown a stent 10 which includes a proximal portion 12 and a distal portion 14 which mate with one another. Proximal portion 12 comprises an endloop construction of hollow members 16, which may be formed from hypo-tube, for example. Distal portion 14 comprises a braided construction of solid members 18, for example, typically a wire, or other filamentary material. In the exemplary configuration illustrated in FIG. 1, solid members 18 of distal portion 14 are secured within hollow members 16 of proximal portion 12 at securement locations 20 to form multi-component stent 10. The detail of such an assembly is seen in FIG. 2.

An exemplary material for forming hollow members 16 of proximal portion 12 is nitinol (a nickel-titanium alloy), and an exemplary material for forming solid members 18 of distal portion 14 is a cobalt-chromium-molybdenum alloy such as that commercially available from Elgiloy Specialty Metals of Elgin, IL., under the trademark Elgiloy®. The present invention, however, is not limited to these materials, and may include any materials, metallic (stainless steel, for example) or non-metallic (polyurethane, for example), that offer desired stent properties including compressibility, expandability, and wear-resistance.

Figure 2:
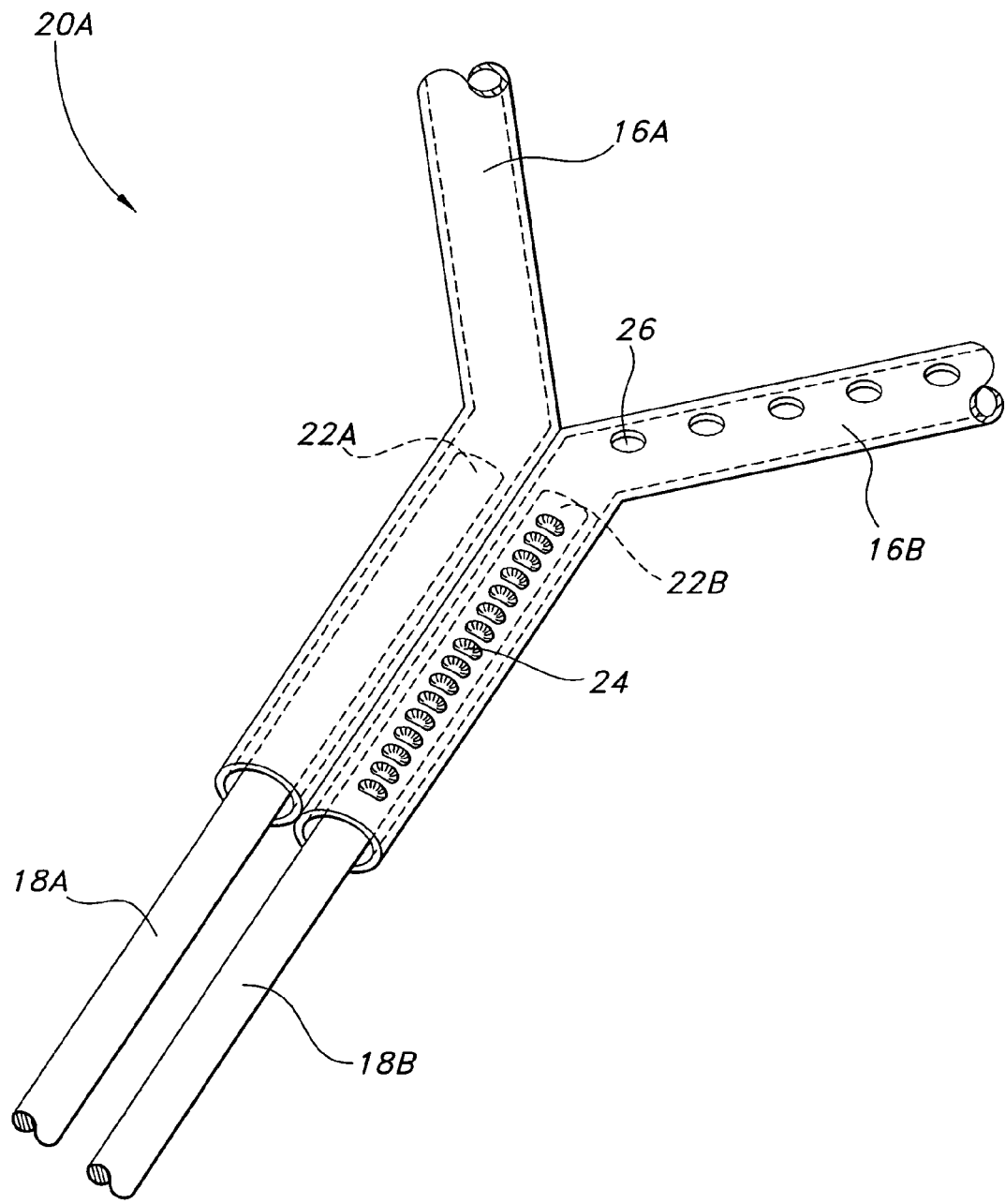
FIG. 2 is a perspective view of two solid stent members secured within two hollow stent members.

FIG. 2 is a detailed perspective view of one of the securement locations 20 of FIG. 1, referred to in FIG. 2 as securement location 20A. Hollow members 16A and 16B terminate in parallel portions and the portions are secured to one another. Solid member 18A is secured within hollow member 16A, and solid member 18B is secured within hollow member 16B. More specifically, end portions 22A and 22B of solid members 18A and 18B, respectively, are tucked within the interior of each respective hollow member 16A and 16B. This enclosed end portion configuration prevents undesirable sharp surfaces at securement location 20A, thereby helping to prevent trauma to the body lumen in which stent 10 is deployed.

Hollow members 16A and 16B are crimped to solid members 18A and 18B, respectively, and then the connections are welded, as represented by weld points 24, to modify the tubing/wire interface. This crimping and welding technique is described in U.S. application Ser. No. 10/748,444 filed Dec. 20, 2003, entitled, "CRIMP AND WELD CONNECTION," which, as stated above, is incorporated herein by reference. The securing means, however, is not limited to a weld. Alternatively, solid members 18A and 18B may be secured within hollow members 16A and 16B, respectively, by soldering, or any other technique that results in sufficient peel strength, shear or tensile strength, and radial strength at and/or around securement location 20A.

Figure 3:
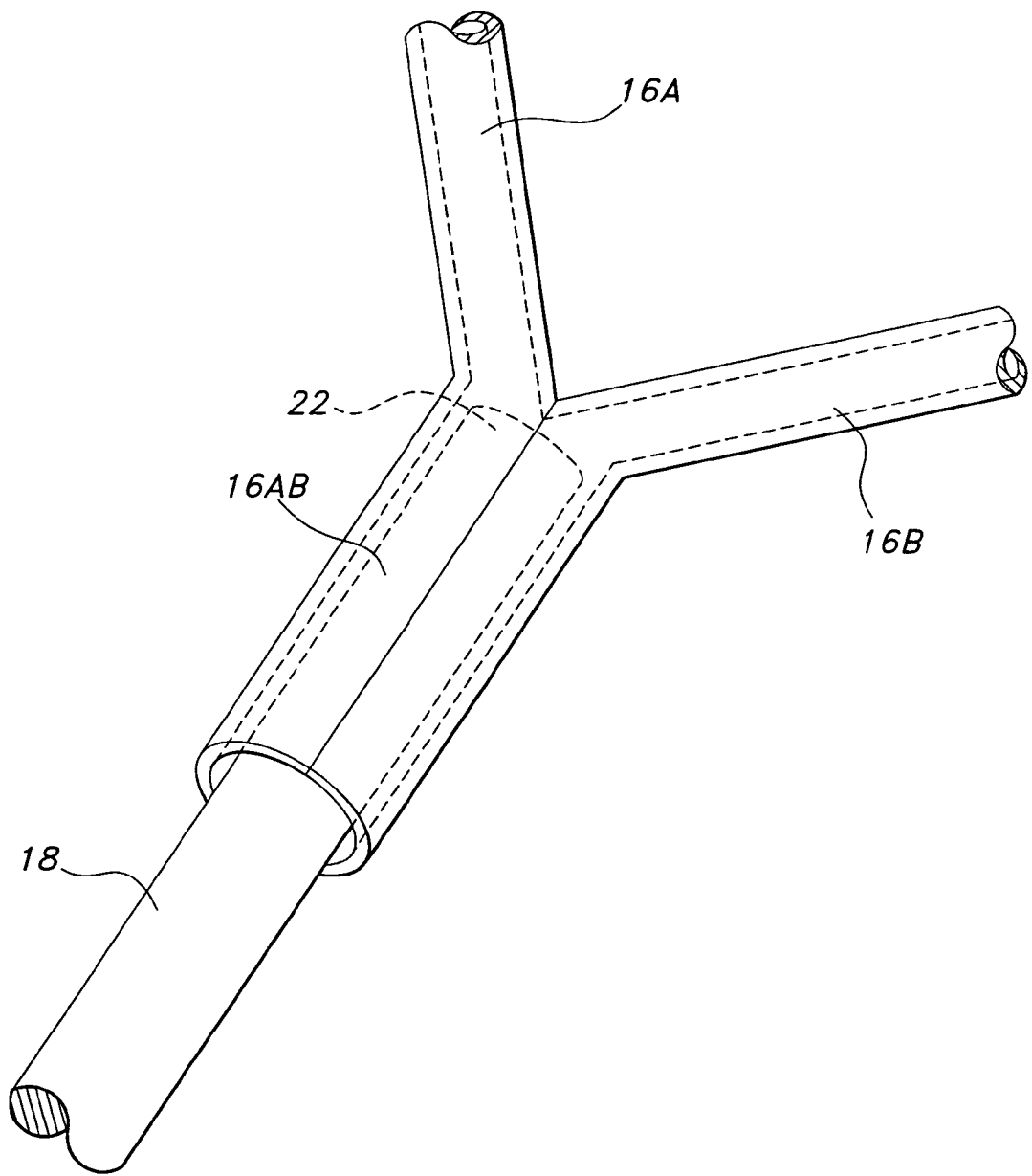
FIG. 3 is a perspective view of an assembly of a solid member secured within two hollow stent members.

For clarity purposes, weld 24 is represented in FIG. 2 only as securing solid member 18B within hollow member 16B. However, it is contemplated that each solid member 18A and 18B is secured within (as illustrated in FIGS. 2, 3, and 5) or secured to (as illustrated in FIGS. 4 and 5) hollow members via a weld, solder, or other means. Similarly, hollow members 16A and 16B may be secured to one another via a weld, solder, or other means. Yet, such securing material is likewise not represented in the figures for clarity purposes.

One or both hollow members 16A and 16B may contain a radiographically differentiable material, such as barium sulfate, or some other imageable material (not shown) to facilitate placement of the stent 10 with radiographic imaging. Furthermore, one or both hollow members 16A and 16B may include openings 26 between the hollow interior of each member 16A and 16B and an exterior thereof, along with a slow-release polymer outer layer (not shown). Such a hollow member 16A and/or 16B may contain a drug for elution through the openings 26 and into the body lumen in which stent 10 is deployed. Moreover, the openings 26 may promote ingrowth of the body lumen in which the stent 10 is deployed, thereby improving fixation and migration resistance of the stent 10.

Again for clarity purposes, openings 26 are represented in FIG. 2 only as part of hollow member 16B. However, any one or more of hollow members 16 may include any number of openings 26 of various shapes and sizes suitable for drug elution.

The braided construction of distal portion 14 of stent 10 (best seen in FIG. 1) is not limited to one wire (solid member 18) per hollow member 16, as illustrated in FIG. 2. In other words, any number of wires 18 may be secured within a hollow member 16, depending upon the desired configuration of the braided stent, the exterior diameter of each individual wire 18, and the interior diameter of the particular hollow member 16.

FIG. 3 illustrates an alternative exemplary configuration of an assembly including hollow stent members. A notable difference from the assembly shown in FIG. 2, however, is that hollow members 16A and 16B are skived. In other words, portions of hollow members 16A and 16B are split open forming open edges, which open edges are then secured to one another to form a larger diameter hollow member combination 16AB. Hollow members 16A and 16B may be secured to one another via a weld, solder, or other means. Such securing material is not represented in the figures for clarity purposes. Hollow member combination 16AB forms a larger interior for accommodating a larger solid member 18 (as shown) or multiple solid members (not shown).

As in the assembly of FIG. 2, hollow member combination 16AB of FIG. 3 is crimped to solid member 18, and then the connection is welded. Similarly, one or both hollow members 16A and 16B may contain a radiographically differentiable material. Furthermore, one or both hollow members 16A and 16B may include openings 26 for drug elution and/or to promote ingrowth.

Figure 4A:
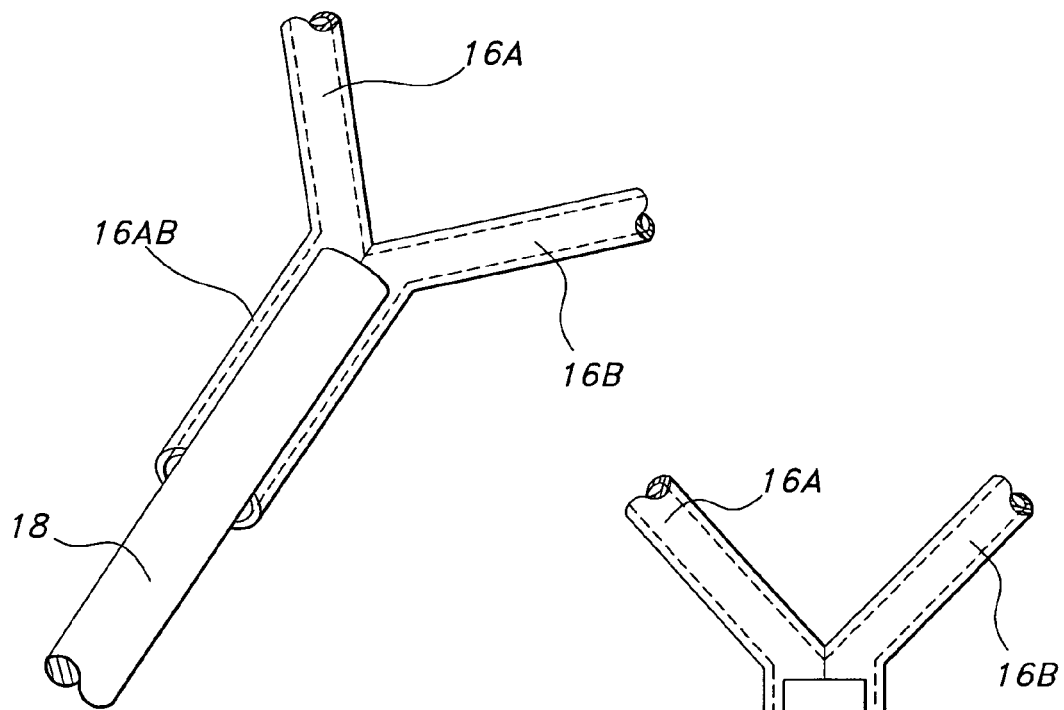
FIG. 4A is a perspective view of an assembly of a solid stent member secured to two mated hollow stent members.
Figure 4B:
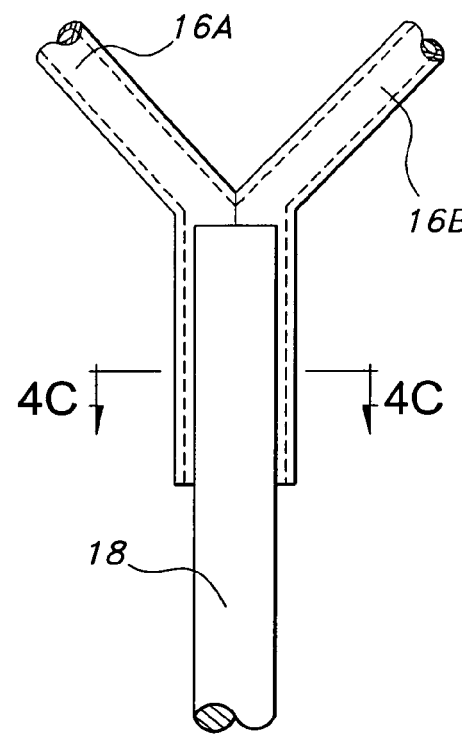
FIG. 4B is a plan view of the embodiment illustrated in FIG. 4A.
Figure 4C:
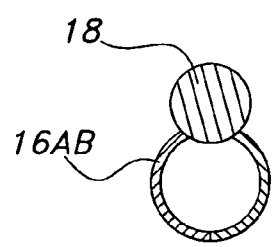
FIG. 4C is a cross-sectional view of the embodiment illustrated in FIG. 4A, showing the solid member secured to the two hollow members.
Figure 5:
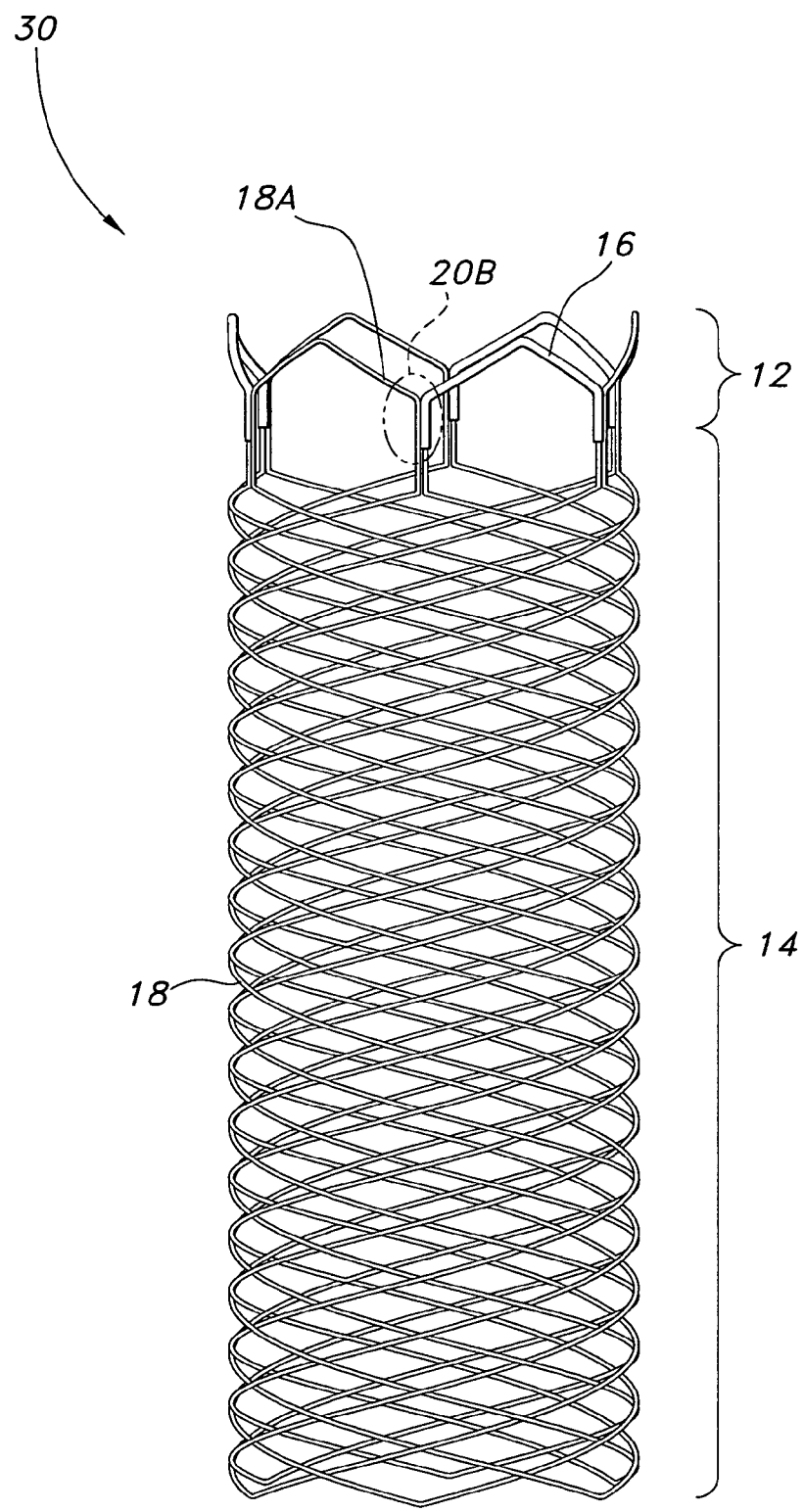
FIG. 5 illustrates another multi-component stent which utilizes hollow stent members as described herein.

FIGS. 4A-4C illustrate yet another alternative configuration of the stent member assembly shown in FIGS. 1 and 2. In this configuration solid member 18 is secured to the exterior of hollow member combination 16AB.

As in the assembly shown in FIG. 3, hollow members 16A and 16B are skived and a portion thereof removed. As in previously described configurations, one or both hollow members 16A and 16B may contain a radiographically differentiable material. Furthermore, one or both hollow members 16A and 16B may include openings 26 for drug elution and/or to promote endothelial ingrowth.

A notable difference from the assembly shown in FIG. 3, however, is that only one pair of open edges of hollow members 16A and 16B are secured to one another. As best seen in FIG. 4C, one pair of open edges is left open for contact with solid member 18. Solid member 18 is secured to the pair of open edges, typically via a weld, solder, or other means (not shown). In this configuration, solid member 18 is a protrusion, and may act as an anchoring device or barb to anchor stent 10 to the body lumen in which stent 10 is deployed.

Figure 6:
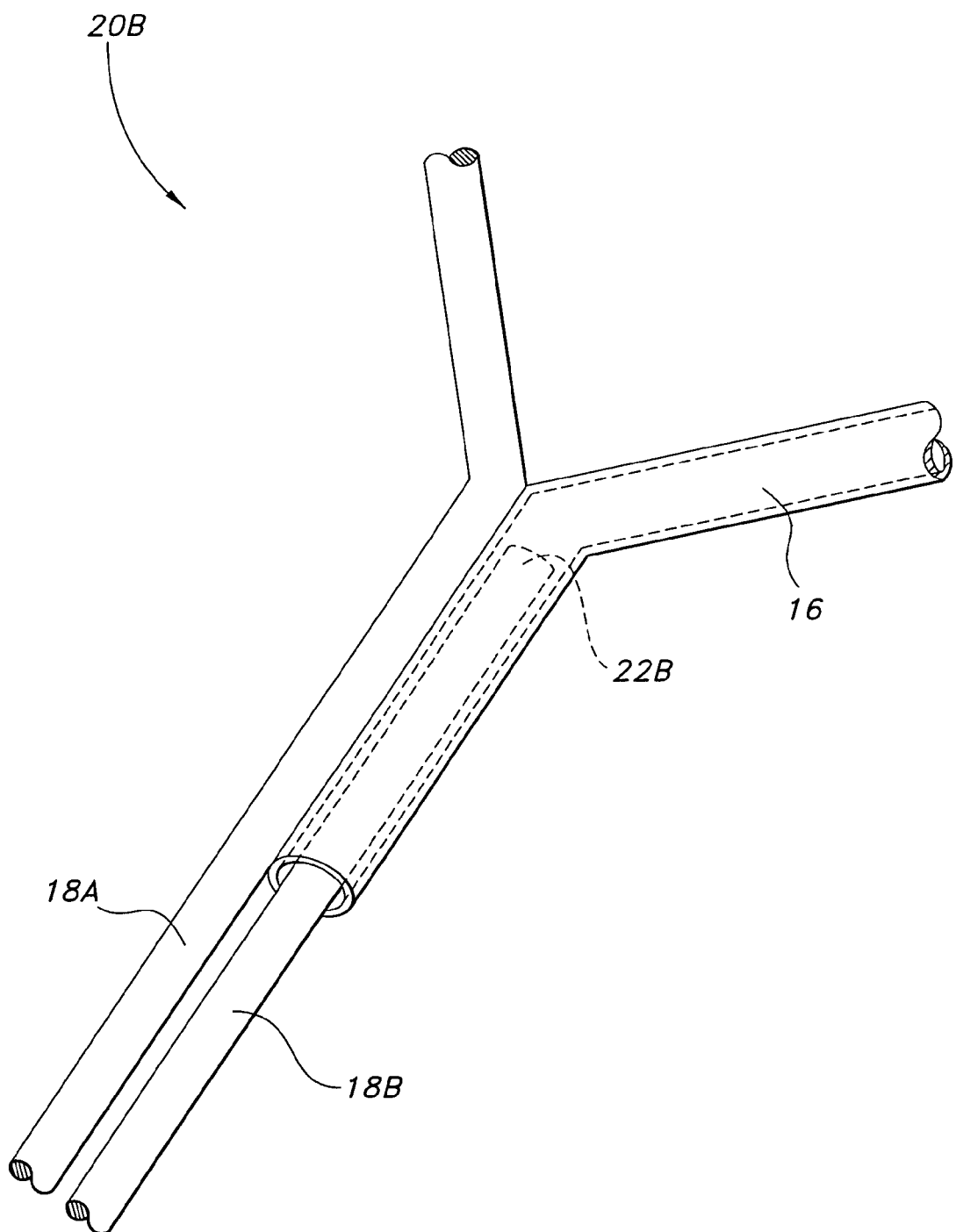
FIG. 6 is a perspective view of a solid stent member secured within a hollow stent member, and another solid member secured to the hollow member externally.

FIG. 5 illustrates another alternative configuration of the assembly shown in FIGS. 1 and 2. In FIG. 5 there is shown a stent 30 which includes a proximal portion 12 and a distal portion 14. Proximal portion 12 comprises an endloop construction of both hollow members 16 and solid members 18. More specifically, distal portion 14 comprises a braided construction of solid members 18 having some members 18B secured within respective hollow members 16, and other members 18A secured to an outer surface of respective hollow members 16, of which a subassembly 20B is illustrated in greater detail in FIG. 6. Each solid member 18A that is secured to an outer surface of a respective hollow member 16 is configured to return toward distal portion 14 (as shown in FIG. 5) and is secured to a respective solid member 18 via a weld, solder, or other means (not shown).

As in the stent member assemblies previously described, hollow member 16 may be crimped to solid member 18B, and then welded. Similarly, hollow member 16 may contain a radiographically differentiable material. Furthermore, hollow member 16 may include openings 26 for drug elution and/or to promote ingrowth.

In the exemplary configuration illustrated in FIG. 5, hollow members 16 and solid members 18A alternate around the circumference of proximal portion 12. The present invention, however, is not limited to such a configuration. For example, the circumference of proximal portion 12 may comprise two hollow members 16 alternating with one solid member 18A. Alternatively, the circumference of proximal portion 12 may comprise only one solid member 16 among solid members 18A. The flexibility of the proximal portion design permits radiographically differentiable material to be contained in selective locations throughout stent 30 to aid in a variety of imaging situations.

While a number of embodiments of the present invention have been shown and described herein, it will be understood that such embodiments are provided by way of example only. Numerous alternatives, variations, changes and substitutions may be devised which are nevertheless within the true spirit and scope of the present invention. Accordingly, it is intended that the appended claims cover all such alternatives, variations, changes, and substitutions.

What is claimed:

1. A stent comprising:
   at least two stent segments that mate with one another;
   at least one of said stent segments being an endloop segment being formed from a plurality of elongated members, each of the plurality of elongated members having a first open end and a second open end and having a hollow tubular cross section extending between the first open end and the second open end; and
   at least another of said stent segments is at least partially formed from a plurality of solid members, each of the solid members having first and second ends;
   wherein each one of the first and second ends of the solid members is fixedly inserted into a respective one of the first and second open ends of the elongated members to resist separation.

2. The stent of claim 1, wherein each of said one or more elongated members terminate in parallel portions and said portions are secured to one another.

3. The stent of claim 1, wherein at least one of said endloop segment contains an imageable material.

4. The stent of claim 1, wherein at least one of said elongated members defines at least one opening between a hollow interior of said elongated member and an exterior thereof.

5. The stent of claim 4, wherein at least one of said elongated members contains a drug for elution through said opening.

6. The stent of claim 1, wherein said solid member is welded to at least one of said one or more elongated members.

7. The stent of claim 6, wherein said solid member is welded within at least one of said elongated members.

8. The stent of claim 1, wherein end portions of at least one of said one or more elongated members are disposed adjacent one another, are open to one another, and are secured to one another to form a larger interior member combination.

9. The stent of claim 8, wherein said end portions are secured to one another to form a hollow interior of larger diameter than said elongated member.

10. The stent of claim 8, wherein said solid member is disposed along and secured to edges of said end portions.

11. The stent of claim 9, wherein said solid member is disposed within said larger diameter hollow interior.

12. The stent of claim 1, wherein each of said one or more elongated members is a hypo-tube.

13. The stent of claim 1, wherein the material of said one or more elongated members is nitinol.

14. The stent of claim 1, wherein the material of said solid members is a cobalt-chromium-molybdenum alloy.

15. The stent of claim 14, wherein the material of said one or more elongated members is nitinol.

16. A stent comprising:
an endloop segment having a first wall being formed from elongated members having a first end, a second end, and a hollow tubular cross section between the first end and the second end; and
another segment having a second wall being at least partially formed from solid members, each solid member,
wherein the first solid end at least one of said solid members is inserted into and fixedly attached to the first end of at least one of said elongated members and the second solid end of the at least one of said solid members is inserted into and fixedly attached to the second end of the at least one of said elongated members to resist separation.

17. A tubular stent having a proximal end and a distal end, said tubular stent comprising:
an endloop segment at said proximal end, said endloop segment being formed from elongated members having hollow tubular cross sections throughout each of the elongated members and each of said elongated members comprising a first end and a second end, wherein said first end and said second end of each of said elongated members extend toward said distal end; and
a braided segment at said distal end, said braided segment comprising solid members and each of said solid members comprising a first solid end and a second solid end, wherein said solid members are formed in a braided configuration and said first solid end and said second solid end of each of said solid members extend toward said proximal end,
wherein said first solid end of one of said solid members is inserted into and fixedly secured to said first end of one of said elongated members and the second solid end of the one of said solid members is inserted into and secured to said second end of the one of said elongated members.

18. A method of forming an atraumatic connection for a multi-component stent wherein the stent comprises one segment being an endloop segment having a first wall being formed exclusively from elongated members having hollow tubular cross sections throughout each of the elongated members and another segment having a second wall being at least partially formed from elongated solid members each elongated solid member having a first end and a second end, said method comprising the steps of:
tucking each of the first end and the second end of one of the solid members within the interior of a first end and a second end one of the elongated members respectively; and
fixedly attaching toe one of the solid members within the one of the elongated members to resist separation.

19. The method of claim 18, wherein said securing step comprises the steps of:
crimping the one of the elongated members to the one of the solid members to form connections between the one of the elongated members and the one of the solid members; and
welding each connection.

20. A tubular stent comprising:
an endloop segment comprising distinct hollow members; and
a second segment, said second segment comprising distinct solid members, wherein said said distinct solid members are secured to said distinct hollow members, wherein each of the distinct hollow members of the endloop segment comprises first and second hollow ends and each of the distinct solid members of the second segment comprises first and second solid ends, and wherein the first solid end of one of the distinct solid members is fixedly
attached within the first hollow end of one of the distinct hollow members and wherein the second solid end of the one of the distinct solid members is fixedly attached with in the second hollow end of the one of the hollow members to resist separation.

21. The tubular stent of claim 20, wherein all of said hollow members are located exclusively in said endloop segment.

22. The tubular stent of claim 20, wherein at least one of said solid members is secured within at least one of said hollow members.

23. A stent comprising:
at least two stent segments that mate with one another;
at least one of said stent segments being an endloop formed from one or more elongated members, each of the one or more elongated members having a first open end and a second open end and having a hollow tubular cross section between the first open end and the second open end; and
at least one of said stent segments being at least partially formed from solid members, each solid member having a first solid end and a second solid end;
wherein the first and second solid ends of each of said solid members are inserted into and fixedly attached to respective first and second open ends of each of the elongated members to resist separation.

* * * * *